United States Patent
Okazaki et al.

(10) Patent No.: US 10,568,492 B2
(45) Date of Patent: Feb. 25, 2020

(54) MEDICAL OBSERVATION DEVICE AND MEDICAL OBSERVATION METHOD

(71) Applicants: SONY CORPORATION, Tokyo (JP); SONY OLYMPUS MEDICAL SOLUTIONS INC., Tokyo (JP)

(72) Inventors: Sakae Okazaki, Tokyo (JP); Toshio Katayama, Kanagawa (JP); Hirotaka Hirano, Gifu (JP); Takahiro Yamamoto, Tokyo (JP)

(73) Assignees: SONY CORPORATION, Tokyo (JP); SONY OLYMPUS MEDICAL SOLUTIONS INC., Tokyo (JP)

( * ) Notice: Subject to any disclaimer, the term of this patent is extended or adjusted under 35 U.S.C. 154(b) by 71 days.

(21) Appl. No.: 15/576,969

(22) PCT Filed: May 12, 2016

(86) PCT No.: PCT/JP2016/064126
§ 371 (c)(1),
(2) Date: Nov. 27, 2017

(87) PCT Pub. No.: WO2017/010157
PCT Pub. Date: Jan. 19, 2017

(65) Prior Publication Data
US 2018/0146844 A1 May 31, 2018

(30) Foreign Application Priority Data
Jul. 15, 2015 (JP) .................................. 2015-141225

(51) Int. Cl.
*A61B 1/00* (2006.01)
*G02B 7/28* (2006.01)
(Continued)

(52) U.S. Cl.
CPC ...... *A61B 1/00188* (2013.01); *A61B 1/00009* (2013.01); *A61B 1/00096* (2013.01);
(Continued)

(58) Field of Classification Search
CPC .............. A61B 1/00188; A61B 1/0638; A61B 1/00096; A61B 90/37; A61B 1/00009;
(Continued)

(56) References Cited

U.S. PATENT DOCUMENTS

| | | | | |
|---|---|---|---|---|
| 2012/0176486 A1* | 7/2012 | Maeda | ............... | A61B 1/00009 348/68 |
| 2013/0184530 A1* | 7/2013 | On | ..................... | A61B 1/00181 600/168 |

(Continued)

FOREIGN PATENT DOCUMENTS

| | | |
|---|---|---|
| JP | 2004-272039 A | 9/2004 |
| JP | 2012-110481 A | 6/2012 |
| WO | 2015/012096 A1 | 1/2015 |

OTHER PUBLICATIONS

Extended European Search Report dated Jan. 8, 2019 in corresponding European Patent Application No. 16824137.0, 7 pages.
(Continued)

*Primary Examiner* — Tony Ko
(74) *Attorney, Agent, or Firm* — Xsensus LLP

(57) ABSTRACT

[Object] To control the focal position of an optical system with a more favorable aspect, in accordance with the band targeted for observation.
[Solution] A medical observation device includes: a computation section that applies, to an imaging signal corresponding to each of a plurality of different spectral components based on a light receiving result regarding observation target light from a subject in vivo from an image sensor, weights of the plurality of spectral components correspond-
(Continued)

ing to a band targeted for observation from among bands in the observation target light, and computes an evaluation value indicating a degree of being in-focus on a basis of the imaging signal to which the weights are applied; and a control section that controls, on a basis of the evaluation value, a position of at least one optical member in an optical system that forms an image of the observation target light from the subject onto the image sensor, and thereby controls a focal position of the optical system.

20 Claims, 6 Drawing Sheets

(51) Int. Cl.
  *G03B 15/00*   (2006.01)
  *G02B 7/36*   (2006.01)
  *A61B 1/06*   (2006.01)
  *A61B 90/00*   (2016.01)
  *A61B 1/04*   (2006.01)
  *G02B 27/40*   (2006.01)
  *A61B 8/00*   (2006.01)
  *A61B 8/08*   (2006.01)

(52) U.S. Cl.
  CPC ............. *A61B 1/042* (2013.01); *A61B 1/043* (2013.01); *A61B 1/0638* (2013.01); *A61B 90/361* (2016.02); *A61B 90/37* (2016.02); *G02B 7/28* (2013.01); *G02B 7/36* (2013.01); *G02B 27/40* (2013.01); *G03B 15/00* (2013.01); *A61B 1/00045* (2013.01); *A61B 8/466* (2013.01); *A61B 8/5207* (2013.01)

(58) Field of Classification Search
  CPC ....... A61B 1/043; A61B 90/361; A61B 1/042; A61B 1/00045; A61B 8/466; A61B 8/5207; G02B 27/40; G02B 7/36; G02B 7/28; G03B 15/00
  See application file for complete search history.

(56) References Cited

U.S. PATENT DOCUMENTS

2015/0080651 A1\*   3/2015   Azuma .................... A61B 1/06
                               600/103
2015/0112128 A1    4/2015   Yoshino
2019/0167083 A1\*   6/2019   Watanabe ................ A61B 1/00

OTHER PUBLICATIONS

International Search Report dated Jul. 19, 2016 in PCT/JP2016/064126 filed May 12, 2016.

\* cited by examiner

MEDICAL OBSERVATION DEVICE AND MEDICAL OBSERVATION METHOD

TECHNICAL FIELD

The present disclosure relates to a medical observation device and a medical observation method.

BACKGROUND ART

Recently, due to advancements in surgical techniques and surgical equipment, surgeries for performing various treatments (also called microsurgery) while observing an affected site with an observation device for medical use, such as an endoscope or a surgical microscope, are coming to be conducted frequently. Also, such observation devices for medical use are not limited to devices that enable optical observation of the affected area, and also include devices that display an image of the affected area captured by an imaging section (camera) or the like as an electronic image on a display such as a monitor.

Also, some imaging sections like the above are provided with an auto focus (AF) function that automatically brings a subject into focus. For example, Patent Literature 1 discloses an example of an endoscopic device provided with an auto focus function.

CITATION LIST

Patent Literature

Patent Literature 1: JP 2012-110481A

DISCLOSURE OF INVENTION

Technical Problem

For the observation of an affected area with a medical observation device such as an endoscope or a surgical microscope, there is known what is called specific light observation, which treats light in a different band from ordinary light (white light) as the target of observation, such as narrow-band imaging (NBI), auto fluorescence imaging (AFI), and infra red imaging (IRI).

Meanwhile, with such specific light observation, depending on the band targeted for observation, misalignment occurs in the position where the optical system is in focus (hereinafter designated the "in-focus position" in some cases), and obtaining a clear subject image is difficult in some cases. Such a phenomenon is known to have a tendency of manifesting more readily in the case of using an optical system (such as a lens) with large chromatic aberration in particular.

Accordingly, the present disclosure proposes a medical observation device and a medical observation method capable of controlling the focal position of an optical system with a more favorable aspect, in accordance with the band targeted for observation.

Solution to Problem

According to the present disclosure, there is provided a medical observation device including: a computation section that applies, to an imaging signal corresponding to each of a plurality of different spectral components based on a light receiving result regarding observation target light from a subject in vivo from an image sensor, weights of the plurality of spectral components corresponding to a band targeted for observation from among bands in the observation target light, and computes an evaluation value indicating a degree of being in-focus on a basis of the imaging signal to which the weights are applied; and a control section that controls, on a basis of the evaluation value, a position of at least one optical member in an optical system that forms an image of the observation target light from the subject onto the image sensor, and thereby controls a focal position of the optical system.

In addition, according to the present disclosure, there is provided a medical observation method that is executed by a processor, the medical observation method including: applying, to an imaging signal corresponding to each of a plurality of different spectral components based on a light receiving result regarding observation target light from a subject in vivo from an image sensor, weights of the plurality of spectral components corresponding to a band targeted for observation from among bands in the observation target light, and computing an evaluation value indicating a degree of being in-focus on a basis of the imaging signal to which the weights are applied; and controlling, on a basis of the evaluation value, a position of at least one optical member in an optical system that forms an image of the observation target light from the subject onto the image sensor, and thereby controlling a focal position of the optical system.

Advantageous Effects of Invention

According to the present disclosure as described above, there is proposed a medical observation device and a medical observation method capable of controlling the focal position of an optical system with a more favorable aspect, in accordance with the band targeted for observation.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
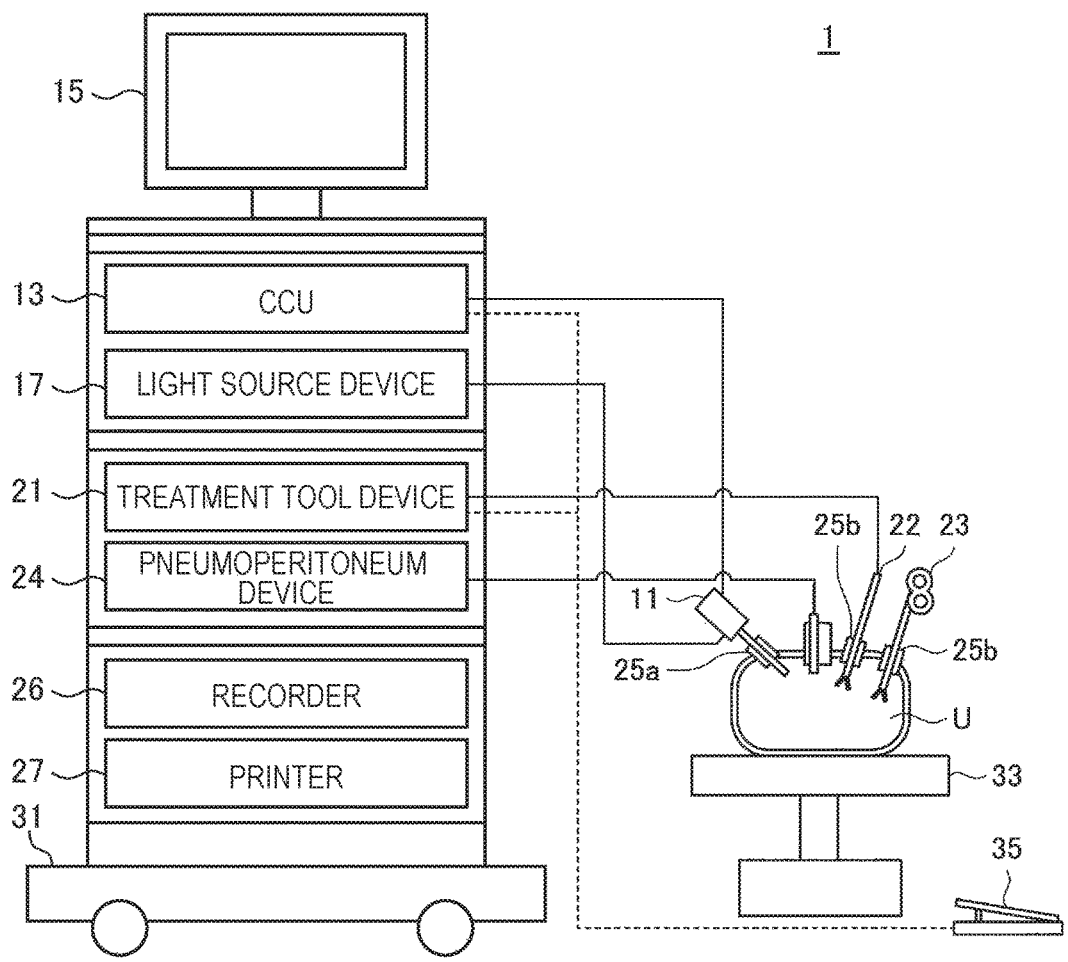
FIG. 1 is an explanatory diagram for explaining an example of a schematic configuration of a system applying a medical observation device according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.

1. System configuration
2. Investigation regarding control of focal position
3. Functional configuration
4. Processes
5. Modifications
6. Applications
7. Hardware configuration
8. Conclusion

1. System Configuration

First, an example of the configuration of a system applying a medical observation device according to the present embodiment will be described with reference to FIG. 1. FIG. 1 is an explanatory diagram for explaining an example of a schematic configuration of a system applying a medical observation device according to the present embodiment.

For example, FIG. 1 illustrates an example of an endoscopic surgical system used in endoscopic surgeries of the abdomen, conducted as a substitute for abdominal surgeries of the past in the medical field. As illustrated in FIG. 1, in an endoscopic surgery of the abdomen, instead of opening up the abdomen by cutting abdominal wall like in the past, hole-opening tools called trocars 25a and 25b are attached to the abdominal wall in several places, and tools such as a laparoscope (hereinafter also called an endoscope) 11, an energy treatment tool 22, and forceps 23 are inserted into the human body through holes provided in the trocars 25a and 25b. Subsequently, a treatment such as excising an affected area U is conducted with the energy treatment tool 22 and the like while viewing in real-time an image of the affected area (such as a tumor) U video-captured by the endoscope 11. Note that the endoscope 11, the energy treatment tool 22, and the forceps 23 are held by a surgeon, an assistant, a scopist, a robot, or the like.

Inside the operating room where such an endoscopic surgery takes place, a cart 31 bearing devices for the endoscopic surgery, a patient bed 33 on which the patient lies, a footswitch 35, and the like are disposed. Also, on the cart 31, devices such as a camera control unit (CCU) 13, a light source device 17, a treatment tool device 21, a pneumoperitoneum device 24, a display device 15, a recorder 26, and a printer 27 are placed as medical equipment, for example.

An image signal of the affected area U captured through an observation optical system of the endoscope 11 is transmitted to the CCU 13 via a camera cable. Note that the CCU 13, besides being connected to the endoscope 11 via the camera cable, may also be connected to the endoscope 11 via a wireless communication link. The CCU 13 performs signal processing on the image signal output from the endoscope 11, and outputs the processed image signal to the display device 15. According to such a configuration, an endoscopic image of the affected area U is displayed on the display device 15.

Note that the CCU 13 may also output the processed image signal to the recorder 26, and thereby cause the recorder 26 to record the endoscopic image of the affected area U as image data (for example, moving image data). Additionally, the CCU 13 may also output the processed image signal to the printer 27, and thereby cause the printer 27 to print out an endoscopic image of the affected area U.

The light source device 17 is connected to the endoscope 11 via a light guide cable, and is able to radiate light onto the affected area U while switching among various wavelengths of light. Note that in some cases, the light radiated from the light source device 17 is also used as auxiliary light, for example.

The treatment tool device 21 corresponds to a high-frequency output device that outputs a high-frequency current to the energy treatment tool 22 that cuts the affected area U using electrical heat, for example.

Additionally, the pneumoperitoneum device 24 is provided with blowing and suction means, and is for blowing air into the patient's body cavity, such as the abdominal region, for example.

The footswitch 35 is configured to control the CCU 13, the treatment tool device 21, or the like by using a foot operation by a person such as the surgeon or an assistant as a trigger signal.

The above thus references FIG. 1 to describe an example of a schematic system configuration of what may be termed an endoscopic surgical system 1 as a system configuration applying a medical observation device according to an embodiment of the present disclosure.

2. Investigation Regarding Control of Focal Position

Next, to more easily understand the features of a medical observation device according to an embodiment of the present disclosure, an overview of operations related to the control of the focal position by an imaging section included in the endoscope 11 or the like will be described, followed by a summary of the challenges of a medical observation device according to the present embodiment.

In some cases, the imaging section included in the endoscope 11 or the like is provided with what is called an auto focus (AF) function, which automatically brings a subject into focus.

Generally, AF methods are broadly classified into the two types of the active method and the passive method. The active method is a method of conducting focusing operations by measuring the distance to the subject by radiating near-infrared light or the like onto the subject and receiving the reflected light therefrom, and moving an optical member included in the optical system to bring the subject into focus on the basis of the measured distance, for example. On the other hand, the passive method is a method of conducting focusing operations not by the self-emission of ranging light or the like, but instead by moving an optical member included in the optical system to bring the subject into focus on the basis of information obtained from a captured subject image.

In addition, methods called the contrast method, the phase difference method, the depth map method, and the triangulation method are generally known as AF methods, for example. All of these methods conduct focusing operations on the basis of information obtained from a captured subject image, and may be applied as passive AF methods in particular.

Figure 2:
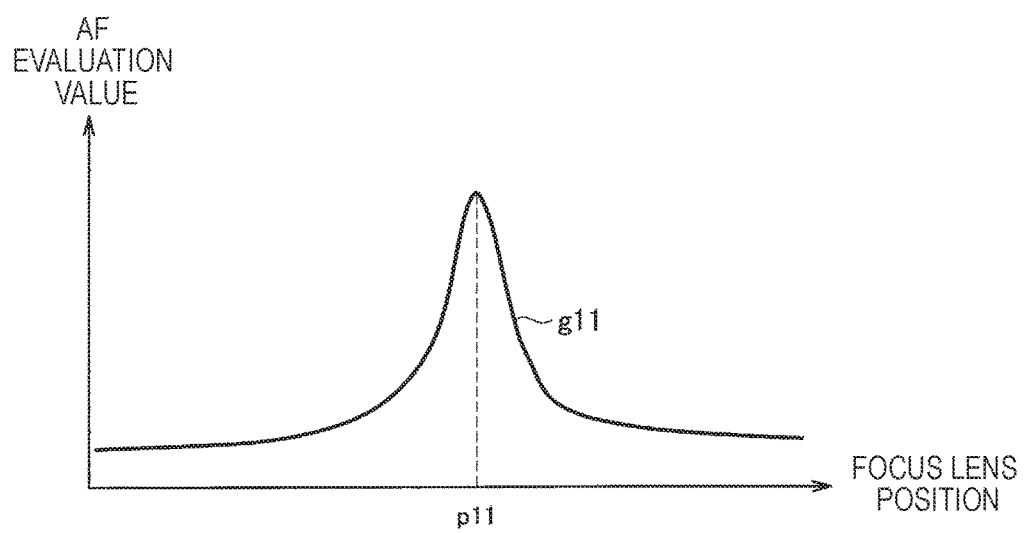
FIG. 2 is an explanatory diagram for explaining the concept of an AF operation by the contrast method.

For example, FIG. 2 is an explanatory diagram for explaining the concept of an AF operation by the contrast method. In FIG. 2, the horizontal axis schematically indicates the position in the optical axis direction of an optical member (in other words, a focus lens) for controlling the focal position (hereinafter designated the "focus lens position" in some cases) among the optical system of the imaging section. Also, the vertical axis indicates an AF evaluation value that the imaging section references to control the focal position. Note that in the contrast method, the contrast of a subject image corresponds to the AF evaluation value. In other words, in FIG. 2, the reference sign g11 schematically indicates an example of change in the contrast of a subject image corresponding to the focus lens position. Also, the reference sign p11 indicates the focus lens position at which the contrast is maximized, or in other words, the in-focus position.

For example, the imaging section evaluates the AF evaluation value (contrast) computed from the subject image while moving the position of the focus lens, and searches for the focus lens position at which the AF evaluation value is maximized (in other words, the in-focus position). Subsequently, the imaging section brings the subject into focus by moving the focus lens to the found in-focus position.

Note that with other methods, although the parameter used as the AF evaluation value and the method of evaluating the AF evaluation value are different, the basic idea of computing an AF evaluation value from a subject image and specifying an in-focus position on the basis of the AF evaluation value is similar to the contrast method. Given the above, in the following description, in the description related to the control of the focal position, the case of applying the contrast method as the method of AF will be described as an example.

Meanwhile, for the observation of an affected area with a medical observation device such as an endoscopic system or a surgical microscope, there is known what is called specific light observation, which treats the component in a band different from ordinary light (white light) as the observation target. For example, narrow-band imaging (NBI) is cited as an example of specific light observation.

With narrow-band imaging, for example light in narrow bands respectively included in the blue light and green light bands is radiated onto the subject as auxiliary light, and from the light reflected back from the subject, an image of the subject is generated on the basis of the light of the green component (green light) and the light of the blue component (blue light). Blue light and green light in particular are absorbed easily by hemoglobin in blood. For this reason, with narrow-band imaging, by utilizing such characteristics, it becomes possible to image blood vessels and the like more clearly, without the use of staining with a pigment or the like, for example.

Also, as other examples of specific light observation, methods such as auto fluorescence imaging (AFI), which observes a target by observing a fluorescence or phosphorescence phenomenon from living or non-living material, and infra red imaging (IRI), which treats infrared light as the target of observation, may be cited. Note that since these observation methods are generally known, detailed description will be reduced or omitted.

With such specific light observation, misalignment occurs in the in-focus position in accordance with the band targeted for observation, and obtaining a clear subject image is difficult in some cases. Such a phenomenon is known to have a tendency of manifesting more readily in the case of using an optical system (such as a lens) with large chromatic aberration in particular.

Figure 3:
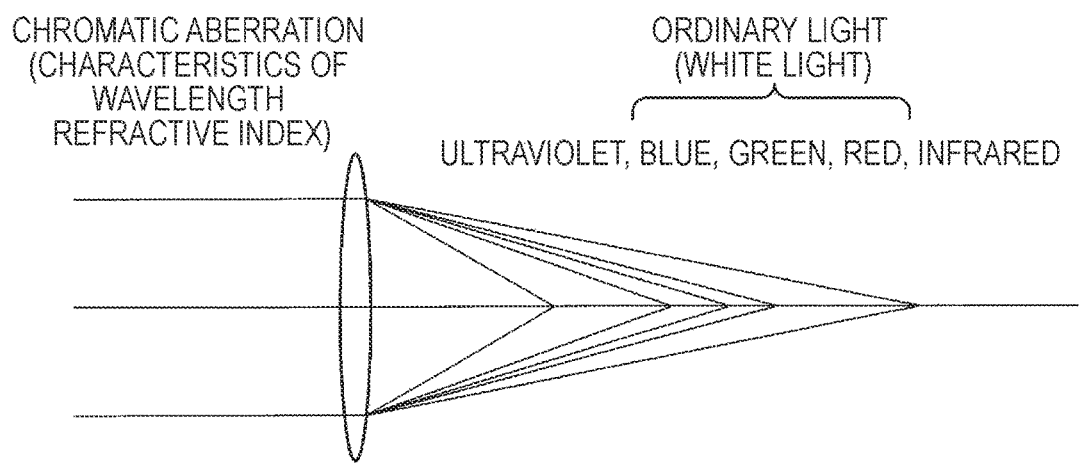
FIG. 3 is an explanatory diagram for explaining the principle by which misalignment occurs in the in-focus position due to chromatic aberration.

For example, FIG. 3 is an explanatory diagram for explaining the principle by which misalignment occurs in the in-focus position due to chromatic aberration. Particularly, in the example illustrated in FIG. 3, to make the description easier to understand, an example of the case of using an optical system (lens) with large chromatic aberration is illustrated schematically.

As illustrated in FIG. 3, in a substance that transmits and refracts light rays (in other words, an optical system such as a lens), the refractive index is not constant, and differs depending on the wavelength (frequency) of the light rays. Specifically, as illustrated in FIG. 3, the shorter the wavelength of the light rays (the higher the frequency of the light rays), the higher the refractive index. For this reason, as illustrated in FIG. 3, for example, compared to ultraviolet light which has a comparatively short wavelength, white light and infrared light which have longer wavelengths than ultraviolet light come into focus at positions farther away from the optical system.

From such characteristics, in the case of treating infrared light as the target of observation, for example, even if the focus lens position is controlled on the basis of an AF evaluation value computed on the basis of a detection result for ordinary light similarly to the case of observing ordinary light (white light), a clearer subject image is not necessarily obtained. Such a phenomenon tends to manifest more readily in an optical system having larger chromatic aberration, as described earlier.

Accordingly, a medical observation device according to the present embodiment proposes a mechanism capable of controlling the focal position of an optical system with a more favorable aspect, in accordance with the band targeted for observation, even in the case of using an optical system with comparatively large chromatic aberration. Note that in the following, a medical observation device according to the present embodiment will be described in further detail.

3. Functional Configuration

Figure 4:
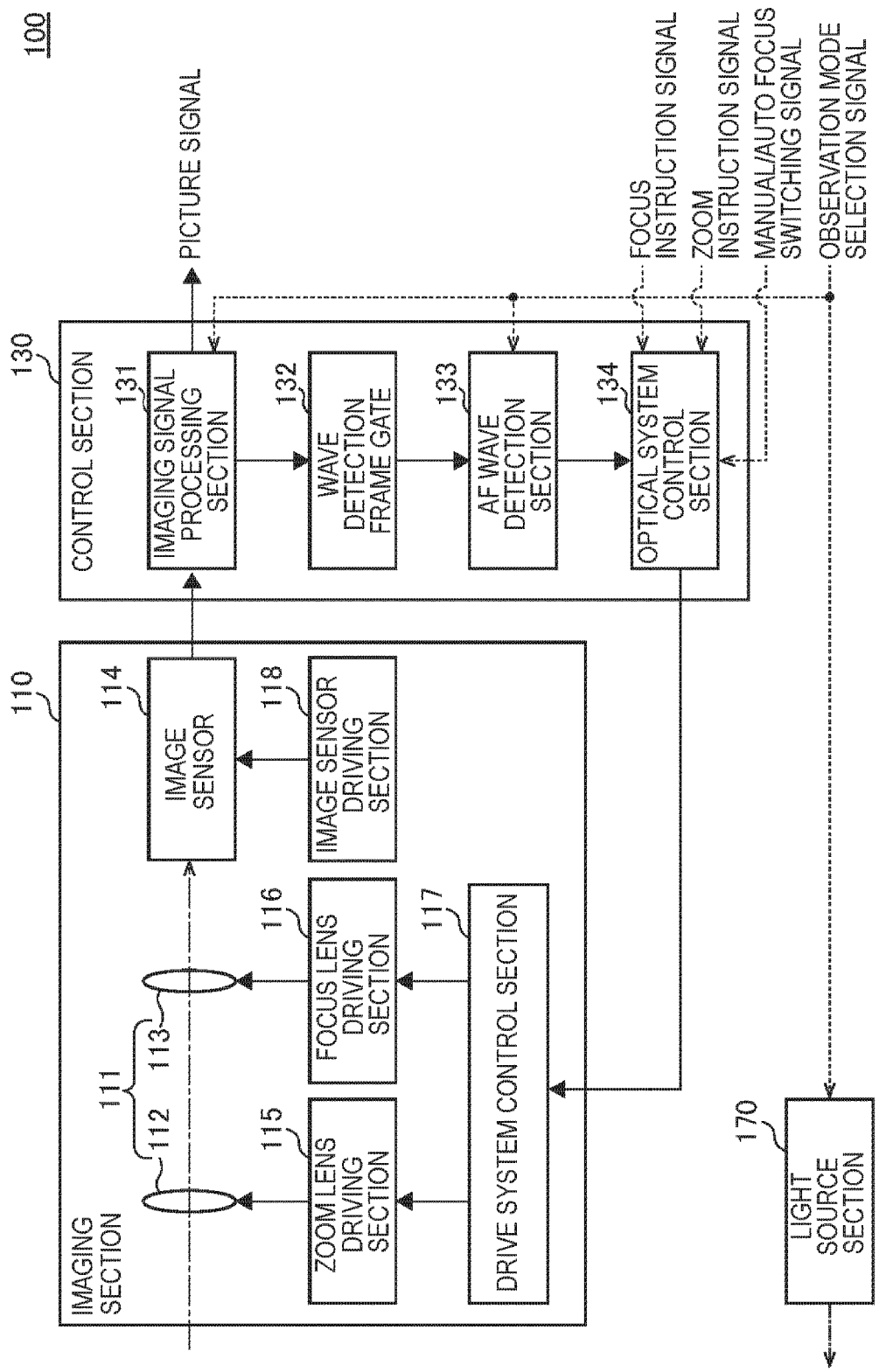
FIG. 4 is a block diagram illustrating an example of a functional configuration of a medical observation device according to the embodiment.

First, FIG. 4 will be referenced to describe an example of a functional configuration of a medical observation device according to the present embodiment. FIG. 4 is a block diagram illustrating an example of a functional configuration of a medical observation device according to the present embodiment, and illustrates an example of a functional configuration with particular focus on a process of capturing an image of a target of observation (test subject) and displaying the image.

As illustrated in FIG. 4, a medical observation device 100 according to the present embodiment includes an imaging section 110 (for example, a camera head) and a control section 130. Additionally, the medical observation device 100 may also include a light source section 170. The medical observation device 100 illustrated in FIG. 4 may be configured as the endoscopic surgical system 1 illustrated in FIG. 1, for example. In other words, the imaging section 110, the control section 130, and the light source section 170 illustrated in FIG. 4 correspond respectively to the endoscope 11, the CCU 13, and the light source device 17 in the endoscopic surgical system 1 illustrated in FIG. 1, for example. Additionally, although not illustrated in FIG. 4, the medical observation device 100 may also include a display section such as a display, which corresponds to the display device 15 in the endoscopic surgical system 1 illustrated in FIG. 1.

The imaging section 110 corresponds to a configuration that captures an image such as a moving image or a still image, like what is commonly called a camera or the like. Specifically, for example, the imaging section 110 includes an imaging optical system (for example, a series of lens groups) 111 and an image sensor 114. Additionally, the imaging section 110 includes a zoom lens driving section 115, a focus lens driving section 116, a drive system control section 117, and an image sensor driving section 118.

The imaging optical system 111 forms an optical image of a subject on the imaging face of the image sensor 114. The imaging optical system 111 includes a zoom lens 112 and a focus lens 113, for example. Note that in the example illustrated in FIG. 4, only the zoom lens 112 and the focus lens 113 are illustrated representatively, but the imaging optical system 111 may also include various types of optical members, such as other lenses and filters. Features such as the type and number of optical members included in the imaging optical system 111 and the optical characteristics of each optical member are adjusted appropriately so that an optical image of a subject is formed on the imaging face of the image sensor 114 by the imaging optical system 111.

The zoom lens 112 is a lens for adjusting the magnification of the imaging optical system 111. The zoom lens 112 is configured to be movable on the optical axis, and by controlling the position on the optical axis of the zoom lens 112, the magnification of the imaging optical system 111 is adjusted. Note that the zoom lens 112 is an example of an optical member for adjusting the magnification of the imaging optical system 111. In other words, it is sufficient to adjust the magnification of the imaging optical system 111 by adjusting the position on the optical axis of at least one optical member included in the imaging optical system 111, and the number and types of optical members configured to be movable to adjust the magnification are not particularly limited.

The focus lens 113 is a lens for adjusting the focal length of the imaging optical system 111. The focus lens 113 is configured to be movable on the optical axis, and by controlling the position on the optical axis of the focus lens 113 (that is, the focus lens position), the focal length of the imaging optical system 111 (in other words, the focal position) is adjusted. Note that the focus lens 113 is an example of an optical member for adjusting the focal length of the imaging optical system 111. In other words, it is sufficient to adjust the focal length of the imaging optical system 111 by adjusting the position on the optical axis of at least one optical member included in the imaging optical system 111, and the number and types of optical members configured to be movable to adjust the focal length are not particularly limited.

For the image sensor 114, a sensor such as a CMOS image sensor or a CCD image sensor may be applied, for example. The image sensor 114 converts the optical image formed on the imaging face into an electrical signal (hereinafter designated the "imaging signal" in some cases) by photoelectric conversion. Specifically, the image sensor 114 according to the present embodiment is provided with light receiving elements (pixels) that receive each of R, G, and B light (spectral components), for example, and converts light from a subject into an imaging signal by photoelectric conversion for each of the R, G, and B spectral components. Note that in the following description, light from the subject received by the image sensor 114 is designated the "observation target light" in some cases. For example, in the ordinary light (white light) imaging, narrow-band imaging, and infra red imaging, reflected light from the subject corresponds to an example of observation target light. Also, in auto fluorescence imaging, fluorescence emitted from the subject (living or non-living material) corresponds to an example of observation target light. Also, in the following description, the imaging signals for each of the R, G, and B spectral components are designated the "R signal", "G signal", and "B signal", respectively, and these are collectively designated the "RGB signal" in some cases. Also, insofar as the image sensor 114 according to the present embodiment can convert observation target light from the subject into an imaging signal by photoelectric conversion for each of multiple spectral components, the spectral components are not necessarily limited to R, G, and B, and may also be yellow (Y), magenta (M), and cyan (C) or the like, for example. Additionally, operations of the image sensor 114 (for example, shutter speed and gain) are controlled by the image sensor driving section 118 described later, for example.

Subsequently, the image sensor 114 outputs the imaging signal for each of the spectral components generated by photoelectric conversion (for example, an RGB signal) to the control section 130. With this arrangement, an imaging signal corresponding to the brightness of each of the spectral components received by the image sensor 114 (that is, the imaging signal for each of the spectral components corresponding to the luminance of the subject image) is output to the control section 130.

The zoom lens driving section 115 includes a motor and a driver circuit that supplies a driving current to the motor, for example, and moves the zoom lens 112 along the optical axis. Operations of the zoom lens driving section 115 are controlled by the drive system control section 117 described later.

The focus lens driving section 116 includes a motor and a driver circuit that supplies a driving current to the motor, for example, and moves the focus lens 113 along the optical axis. Operations of the focus lens driving section 116 are controlled by the drive system control section 117 described later.

The drive system control section 117 includes any of various types of processors, such as a central processing unit (CPU) or a digital signal processor (DSP), or a microcontroller on which a processor is mounted together with a storage element such as memory. The drive system control section 117 controls the operations of the zoom lens driving section 115 and the focus lens driving section 116. The drive system control section 117 may also include any of various types of integrated circuits, such as a field-programmable gate array (FPGA), a driver integrated circuit (IC), and/or a dedicated large-scale integration (LSI) chip (that is, an application-specific integrated circuit (ASIC)). The functions of the drive system control section 117 may be realized by having a processor included in the drive system control section 117 execute computational processing in accordance with a certain program.

As a specific example, the drive system control section 117 controls the driving of the zoom lens driving section 115 on the basis of information indicating a movement direction and a movement amount of the zoom lens 112, which is transmitted from an optical system control section 134 of the control section 130 described later. With this arrangement, the zoom lens 112 moves by just the movement amount in the movement direction, and the magnification of the imaging optical system 111 is adjusted. Note that in the case in which another optical member besides the zoom lens 112 is also configured to be movable to adjust the magnification of the imaging optical system 111, the position of such another optical member may also be controlled by the zoom lens driving section 115 on the basis of control from the drive system control section 117.

Also, as another example, the drive system control section 117 controls the driving of the focus lens driving section 116 on the basis of information indicating a movement direction and a movement amount of the focus lens 113, which is transmitted from the optical system control section 134. With this arrangement, the focus lens 113 moves by just the movement amount in the movement direction, and the focal length of the imaging optical system 111 is adjusted. Note that in the case in which another optical member besides the focus lens 113 is also configured to be movable to adjust the focal length of the imaging optical system 111, the position of such another optical member may also be controlled by the focus lens driving section 116 on the basis of control from the drive system control section 117.

Note that in the example illustrated in FIG. 4, the drive system control section 117 is provided in the imaging section 110, but the drive system control section 117 may also be provided outside of the imaging section 110 (for example, in the control section 130).

The image sensor driving section 118 corresponds to a driver for driving the image sensor 114. The image sensor driving section 118 supplies a driving signal to the image sensor 114 at certain timings, thereby causing the image sensor 114 to execute operations such as imaging operations and reset operations at certain timings, and to acquire an imaging signal corresponding to a subject image. With this arrangement, the shutter speed of the image sensor 114 is controlled. In addition, the image sensor driving section 118 may also control the gain applied to a captured image signal in the image sensor 114.

Note that, although omitted from illustration, an image sensor driving control section that controls the operations of the image sensor driving section 118 may be provided in the imaging section 110 or the control section 130. The image sensor driving control section includes any of various types of processors, such as a CPU or DSP, or a microcontroller or the like, and by indicating to the image sensor driving section 118 the timings at which to supply the driving signal described above to the image sensor 114, controls the driving of the image sensor 114 via the image sensor driving section 118. In addition, the image sensor driving control section may also indicate to the image sensor driving section 118 a gain that the image sensor 114 is to apply to the imaging signal, and thereby control the operations of the image sensor 114 via the image sensor driving section 118. Note that the functions of the image sensor driving control section may be realized by having a processor included in the image sensor driving control section execute computational processing in accordance with a certain program.

The control section 130 includes an imaging signal processing section 131, a wave detection frame gate 132, an AF wave detection section 133, and an optical system control section 134. The control section 130 may include any of various types of processors, such as a CPU or DSP, or a microcontroller or the like.

The imaging signal processing section 131 executes various types of signal processing, such as linear matrix processing, white balance processing, and gamma correction processing, (for example, onto the imaging signal (for example, an RGB signal) for each of the spectral components generated by photoelectric conversion in the image sensor 114. Additionally, the imaging signal processing section 131 performs various types of correction processing, such as tonal correction and luminance correction, and image processing for specific purposes, such as video signal generation or an encoding process, on the imaging signal obtained after performing the various types of signal processing. By control like the above, the imaging signal processing section 131 executes what is called a development process, such as adjustment of the brightness of the subject image, adjustment of the white balance, and color reproduction, on the acquired imaging signal, and generates a picture signal.

As a specific example, an example of a process for adjusting the white balance will be described below. For example, it is assumed that R, G, and B are the respective luminance components of the RGB signal targeted for white balance adjustment (for example, an imaging signal output from the image sensor 114), and it is assumed that $m_{30}$, $m_{40}$, and $m_{50}$ are the respective correction coefficients to apply to the RGB signal to adjust the white balance. Herein, provided that $R_1$, $G_1$, and $B_1$ are the respective luminance components of the RGB signal after white balance adjustment, the imaging signal processing section 131 computes $R_1$, $G_1$, and $B_1$ on the basis of the formulas labeled (Formula 1) to (Formula 3) below. Note that the correction coefficients $m_{30}$, $m_{40}$ and $m_{50}$ are set in advance in accordance with a selected mode for white balance adjustment (in other words, a color temperature), for example.

[Math. 1]

$$R_1 = m_{30} \cdot R \quad \text{(Formula 1)}$$

$$G_1 = m_{40} \cdot G \quad \text{(Formula 2)}$$

$$B_1 = m_{50} \cdot B \quad \text{(Formula 3)}$$

Also, as another example, an example of a process for color reproduction will be described below. The imaging signal processing section 131 executes the color reproduction process by performing a correction process based on parameters set in advance for color reproduction (hereinafter designated the "color reproduction matrix" in some cases) on the respective luminance components R, G, and B of the RGB signal. Herein, provided that $R_2$, $G_2$, and $B_2$ are the respective luminance components of the RGB signal after the color reproduction process, and provided that $M_1$ is the color reproduction matrix, the imaging signal processing section 131 computes $R_2$, $G_2$, and $B_2$ on the basis of the formula labeled (Formula 4) below. Note that the respective correction coefficients $m_{00}$ to $m_{02}$, $m_{10}$ to $m_{12}$, and $m_{20}$ to $m_{22}$ in the color reproduction matrix $M_1$ are set in advance in accordance with the content of the color reproduction process.

[Math. 2]

$$\begin{pmatrix} R_2 \\ G_2 \\ B_2 \end{pmatrix} = M_1 \begin{pmatrix} R \\ G \\ B \end{pmatrix} = \begin{pmatrix} m_{00} & m_{01} & m_{02} \\ m_{10} & m_{11} & m_{12} \\ m_{20} & m_{21} & m_{22} \end{pmatrix} \begin{pmatrix} R \\ G \\ B \end{pmatrix} \quad \text{(Formula 4)}$$

Additionally, by the color reproduction process, the imaging signal processing section 131 may also transform the imaging signal for each of the spectral components targeted by the color reproduction process into an imaging signal based on another color space. As a specific example, the imaging signal processing section 131 may transform an RGB signal into components in YCbCr space, which is based on a luminance component Y and chrominance components Cb and Cr. In this case, provided that $M_2$ is a color reproduction matrix for transforming an RGB signal into components in YCbCr space, the imaging signal processing section 131 computes the luminance component Y and the chrominance components Cb and Cr in YCbCr space on the basis of the formula labeled (Formula 5) below

[Math. 3]

$$\begin{pmatrix} Y \\ Cb \\ Cr \end{pmatrix} = M_2 \begin{pmatrix} R \\ G \\ B \end{pmatrix} = \begin{pmatrix} m_{60} & m_{61} & m_{62} \\ m_{70} & m_{71} & m_{72} \\ m_{80} & m_{81} & m_{82} \end{pmatrix} \begin{pmatrix} R \\ G \\ B \end{pmatrix} \quad \text{(Formula 5)}$$

Additionally, the imaging signal processing section 131 may also apply multiple processes among the white balance adjustment and the color reproduction process described above to the imaging signal for each of the spectral components output from the image sensor 114 (for example, an RGB signal). As a specific example, the imaging signal processing section 131 may apply a process related to white balance adjustment to an RGB signal output from the image sensor 114, and perform a color reproduction process on the basis of the color reproduction matrix $M_1$ on the luminance components ($R_1$, $G_1$, $B_1$) of the RGB signal after white balance adjustment. Also, as another example, the imaging signal processing section 131 may perform a color reproduction process on the basis of the color reproduction matrix $M_1$ on an RGB signal output from the image sensor 114, and transform the luminance components ($R_2$, $G_2$, $B_2$) of the RGB signal after the color reproduction process into components in YCbCr space on the basis of the color reproduction matrix $M_2$.

Note that the medical observation device 100 according to the present embodiment, in addition to observation of a subject image on the basis of ordinary light (white light), may also be configured to be able to selectively switch among and execute various types of specific light observation such as narrow-band imaging, auto fluorescence imaging, and infra red imaging, for example. In this case, for example, the imaging signal processing section 131 may also perform a development process (that is, various types of signal processing and various types of image 26 processing) on the imaging signal in accordance with a mode corresponding to the selected observation method (hereinafter designated the "observation mode" in some cases).

Specifically, an observation mode selection signal that indicates an observation mode selected by the surgeon (user) via any of various types of input sections (not illustrated) which are provided on the medical observation device 100, such as buttons, a touch panel, or switches, for example, may be input from such an input section into the imaging signal processing section 131. In this case, on the basis of the input observation mode selection signal, the imaging signal processing section 131 may identify the observation mode selected by the surgeon, and generate a picture signal by performing a development process corresponding to the observation mode identification result on the imaging signal.

As a more specific example, by applying a filter corresponding to the selected observation mode (for example, a bandpass filter) to an acquired imaging signal (for example, an RGB signal), the imaging signal processing section 131 may extract from the imaging signal a component in a band targeted for observation in the observation mode.

In addition, the imaging signal processing section 131 may also switch the content of the white balance adjustment and color reproduction process described above in accordance with the selected observation mode. In this case, for example, the imaging signal processing section 131 may switch the correction coefficients $m_{30}$, $m_{40}$, and $m_{50}$, or the color reproduction matrix $M_1$ or $M_2$ to apply, in accordance with the selected observation mode.

Subsequently, the imaging signal processing section 131 outputs the generated picture signal to a display section such as a display, for example. With this arrangement, a picture of the subject based on the picture signal is displayed on the display section, and the surgeon (user) becomes able to observe a picture of the subject, that is, the affected area.

In addition, the imaging signal processing section 131 outputs an imaging imaging signal for each of the spectral components output from the image sensor 114 (for example, an RGB signal) to the AF wave detection section 133 via the wave detection frame gate 132.

The wave detection frame gate 132 receives the imaging signal for each of the spectral components (for example, an RGB signal) from the imaging signal processing section 131, and outputs, to the AF wave detection section 133 positioned downstream, an imaging signal for each of the spectral components corresponding to the light receiving elements (pixels) in a certain region of the image sensor 114 (hereinafter designated the "AF wave detection frame" in some cases).

Figure 5:
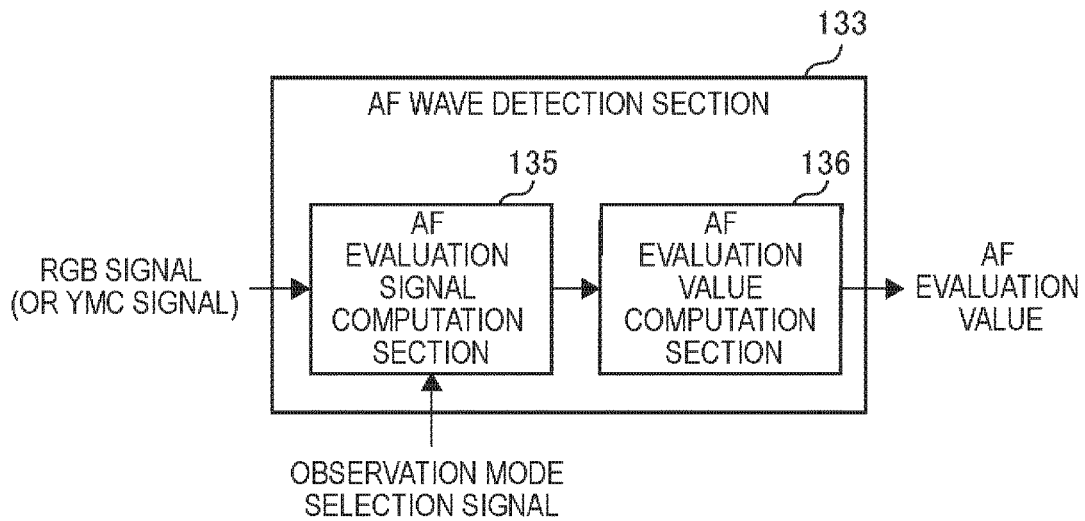
FIG. 5 is a block diagram illustrating an example of a functional configuration of an AF wave detection section.

The AF wave detection section 133 acquires the imaging signal for each of the spectral components from the wave detection frame gate 132. On the basis of the acquired imaging signal, the AF wave detection section 133 computes an AF evaluation value for realizing the AF function, and outputs the computed AF evaluation value to the optical system control section 134 described later. Note that, even in a case of using an imaging optical system 111 having comparatively large chromatic aberration, for example, the AF wave detection section 133 according to the present embodiment computes an AF evaluation value in accordance with the band targeted for observation, to enable control of the focal position of the imaging optical system 111 in a more favorable aspect in accordance with the band of the observation target. Accordingly, in the following, FIG. 5 will be referenced to describe the AF wave detection section 133 in detail. FIG. 5 is a block diagram illustrating an example of a functional configuration of the AF wave detection section 133.

As illustrated in FIG. 5, the AF wave detection section 133 includes an AF evaluation signal computation section 135 and an AF evaluation value computation section 136.

The AF evaluation signal computation section 135 acquires, from an input section, an observation mode selection signal indicating an observation mode selected by the surgeon (user), for example, and on the basis of the acquired observation mode selection signal, recognizes the band targeted for observation.

The AF evaluation signal computation section 135 acquires an imaging signal for each of the spectral components from the wave detection frame gate 132, and with respect to the acquired imaging signal, weights the spectral components in accordance with the band targeted for observation. For example, it is assumed that R, G, and B are the respective luminance components of the RGB signal serving as a target, and it is assumed that r, g, and b are coefficients based on weights for R, G, and B in accordance with the band targeted for observation. At this point, the AF evaluation signal computation section 135 computes an imaging signal L for computing an AF evaluation value (hereinafter designated the "AF evaluation signal" in some cases) on the basis of the formula labeled (Formula 6) below.

[Math. 4]

$$L = r \times R + g \times G + b \times B \qquad \text{(Formula 6)}$$

Note that the coefficients for weighting spectral components like r, g, and b indicated in (Formula 6) (hereinafter designated the "AF evaluation signal coefficients" in some cases) may be computed for each observation mode and stored in advance in a storage area readable by the AF evaluation signal computation section 135, for example. With this arrangement, it is sufficient for the AF evaluation signal computation section. 135 to generate an AF evaluation signal by reading out from the storage area the AF evaluation signal coefficients corresponding to the selected observation mode, and applying the read-out AF evaluation signal coefficients to the acquired imaging signal for each of the spectral components.

As a more specific example, in the case in which infra red imaging, which treats infrared light as the observation target from among the observation target light from the subject, is selected, AF evaluation signal coefficients r, g, and b corresponding to infra red imaging may be set so that infrared light is emphasized more strongly. Similarly, in the case in which narrow-band imaging, which treats green light and blue light as the observation target from among the observation target light from the subject, is selected, AF evaluation signal coefficients r, g, and b corresponding to narrow-band imaging may be set so that the G signal and the B signal are emphasized more strongly. Note that it is sufficient for the AF evaluation signal coefficients corresponding to an observation mode to be computed in advance on the basis of prior experiment or the like so that a component in a band targeted for observation in the relevant observation mode is emphasized more strongly, for example.

Also, as another example, the AF evaluation signal computation section 135 may also decide the AF evaluation signal coefficients in accordance with the surgical procedure of a surgery in which a subject is imaged. In this case, for example, for each surgical procedure, AF evaluation signal coefficients may be computed so that a component in a band targeted for observation in the relevant surgical procedure is emphasized more strongly, and may be stored in advance in a certain storage area. In addition, the AF evaluation signal computation section 135 acquires, from an input section, a selection signal indicating the surgical procedure of a surgery selected by the surgeon (user), for example, and on the basis of the acquired selection signal, identifies the selected surgical procedure. Subsequently, the AF evaluation signal computation section 135 may read out the AF evaluation signal coefficients corresponding to the identified surgical procedure from the certain storage area. Obviously, the example indicated above is merely one example, and the units of management of AF evaluation signal coefficients may be changed appropriately in accordance with the method of operating the medical observation device 100. As a specific example, the AF evaluation signal computation section 135 may decide the AF evaluation signal coefficients in accordance with a clinical department in which a subject is imaged by utilizing the medical observation device 100.

Additionally, the AF evaluation signal computation section 135 may also compute AF evaluation signal coefficients in accordance with the content of the development process that the imaging signal processing section 131 applies to the imaging signal. Note that details about this operation will be separately described as a modification later.

Subsequently, the AF evaluation signal computation section 135 outputs the computed AF evaluation signal to the AF evaluation value computation section 136.

The AF evaluation value computation section 136 acquires the AF evaluation signal from the AF evaluation signal computation section 135, and computes an AF evaluation value on the basis of the acquired AF evaluation signal. As a specific example, in the case in which the AF method is the contrast method, the AF evaluation value computation section 136 computes a contrast on the basis of the acquired AF evaluation signal. More specifically, the AF evaluation value computation section 136 computes the AF evaluation value (contrast) as a sum over all pixels (light receiving elements) inside the AF wave detection frame by using secondary differentiation (Laplacian) using the luminance signal. Note that generally, in the case of being in focus, differences in the luminance signal between adjacent pixels are greater, and thus the contrast is greater, compared to the case of not being in focus.

Note that the method of computing the AF evaluation value indicated above is merely one example, and as described above, the method of computing the AF evaluation value is different depending on the AF method.

Subsequently, the AF evaluation value computation section 136 outputs the computed AF evaluation value to the optical system control section 134 (see FIG. 4).

At this point, FIG. 4 will be referenced again. The optical system control section 134 controls the position of each optical member (for example, the zoom lens 112 or the focus lens 113) included in the imaging optical system 111 of the imaging section 110, and thereby controls focusing operations and zoom operations of the imaging section 110.

For example, an instruction signal for conducting a zoom operation (zoom instruction signal) may be input into the optical system control section 134 by the surgeon (user). The zoom instruction signal is input via any of various types of input sections (not illustrated) which are provided on the medical observation device 100, such as a switch, for example. A zoom instruction signal also includes an instruction regarding the magnification, and on the basis of the zoom instruction signal, the optical system control section 134 decides the movement direction and the movement amount of the zoom lens 112 by which the indicated magnification may be realized, and outputs information indicating the movement direction and the movement amount to the drive system control section 117. The drive system control section 117 receives this information, and via the zoom lens driving section 115, causes the zoom lens 112 to move in the decided movement direction by the decided movement amount. With this arrangement, the magnification of the imaging optical system 111 is adjusted in accordance with an instruction from the surgeon. Note that in the case in which another optical member besides the zoom lens 112 is also configured to be movable to adjust the magnification of the imaging optical system 111, the optical system control section 134 may also decide a movement direction and a movement amount on the optical axis of the other optical member as well.

Also, as another example, the optical system control section 134 may compute the movement direction and the movement amount of the focus lens 113 by which the imaging section 110 controls the focal length of the imaging optical system 111 (for example, conducts a focusing operation).

As a specific example, the optical system control section 134 may be configured to be able to selectively switch between a manual focus (MF) function that controls the focal length on the basis of an instruction from the surgeon (user), and an auto focus (AF) function that automatically brings a subject into focus. In this case, an instruction signal for selectively switching between the MF function and the AF function (manual/auto focus switching signal) may be input into the optical system control section 134 by the surgeon (user). The manual/auto focus switching signal is input via any of various types of input sections (not illustrated) which are provided on the medical observation device 100, such as a switch, for example. On the basis of the manual/auto focus switching signal, the optical system control section 134 switches the method of deciding the movement direction and the movement amount of the focus lens 113.

For example, in the case in which the MF function is selected, an instruction signal for controlling the focal length of the imaging optical system 111 (focus instruction signal) may be input into the optical system control section 134 by the surgeon (user). The focus instruction signal is input via any of various types of input sections (not illustrated) which are provided on the medical observation device 100, such as a switch, for example. For example, a focus instruction signal also includes an instruction regarding the focal length, and on the basis of the focus instruction signal, the optical system control section 134 decides the movement direction and the movement amount of the focus lens 113 by which the indicated focal length may be realized, and outputs information indicating the movement direction and the movement amount to the drive system control section 117. The drive system control section 117 receives this information, and via the focus lens driving section 116, causes the focus lens 113 to move in the decided movement direction by the decided movement amount. With this arrangement, the focal length of the imaging optical system 111 is adjusted in accordance with an instruction from the surgeon. Note that in the case in which another optical member besides the focus lens 113 is also configured to be movable to adjust the focal length of the imaging optical system 111, the optical system control section 134 may also decide a movement amount on the optical axis of the other optical member as well.

Also, in the case in which the AF function is selected, the optical system control section 134 decides the movement direction and the movement amount of the focus lens 113 on the basis of the AF evaluation value (for example, contrast) output from the AF wave detection section 133. Specifically, the optical system control section 134 controls the position of the focus lens 113 via the drive system control section 117, while also comparing the AF evaluation values output from the AF wave detection section 133 before and after the movement of the focus lens 113. Subsequently, on the basis of the AF evaluation value comparison result, the optical system control section 134 decides a movement direction and a movement amount of the focus lens 113 so that the focus lens 113 moves on the optical axis in a direction in which the AF evaluation value increases. Note that when initially moving the focus lens 113 (that is, in the case in which an AF evaluation value from before the movement to compare against does not exist), it is sufficient to decide a movement direction and a movement amount of the focus lens 113 to move the focus lens 113 by a certain distance in a certain direction set in advance.

Subsequently, the optical system control section 134 outputs information indicating the movement direction and the movement amount of the focus lens 113 decided on the basis of the AF evaluation value comparison result to the drive system control section 117. The drive system control section 117 receives this information, and via the focus lens driving section 116, causes the focus lens 113 to move in the decided movement direction by the decided movement amount.

Thereafter, by repeatedly executing the series of processes described above (that is, the process related to deciding a movement direction and a movement amount based on an AF evaluation value comparison result, and a process related to moving the focus lens 113 in accordance with the movement direction and the movement amount), an AF operation is executed. In other words, the AF wave detection section 133 re-computes an AF evaluation value on the basis of an imaging signal obtained by the image sensor 114 after the movement of the focus lens 113, and the optical system control section 134 decides a movement direction and a movement amount of the focus lens 113 on the basis of the computed AF evaluation value. Subsequently, the drive system control section 117 moves the focus lens 113 on the basis of the decided movement direction and movement amount. By repeatedly executing these processes, ultimately the focus lens 113 is moved to a position at which the AF evaluation value (for example, the contrast of the subject image) is maximized, the subject is brought into focus, and the series of processes related to the AF operation ends.

Note that the case in which the MF function is selected is also similar in that, in the case in which another optical member besides the focus lens 113 is also configured to be movable to adjust the focal length of the imaging optical system 111, the optical system control section 134 may also decide a movement amount on the optical axis of the other optical member as well.

Note that the processes related to the AF operation described above are merely one example, and insofar as an AF operation can be realized on the basis of an AF evaluation value, the type of parameter used as the AF evaluation value and the content of the processes related to the AF operation are not particularly limited.

The light source section 170 is provided with multiple light sources having different bands of emitted light, for example, and is configured to be able to selectively switch the light source. For example, an observation mode selection signal that indicates an observation mode selected via any of various types of input sections (not illustrated) which are provided on the medical observation device 100, such as buttons, a touch panel, or switches, for example, is input from such an input section into the light source section 170. On the basis of the input observation mode selection signal, the light source section 170 causes a light source corresponding to the selected observation mode to radiate auxiliary light. According to such a configuration, auxiliary light corresponding to the selected observation mode is radiated from the corresponding light source towards the subject.

Also, as another example, the light source section 170 may also be configured to have a removable light source corresponding to the observation mode. In this case, for example, in the case in which an observation mode selection signal indicating that an observation mode corresponding to the installed light source is selected is input, it is sufficient for the light source section 170 to cause that light source to radiate auxiliary light.

The above thus describes an example of a functional configuration of a medical observation device according to the present embodiment with reference to FIGS. 4 and 5.

4. Processes

Figure 6:
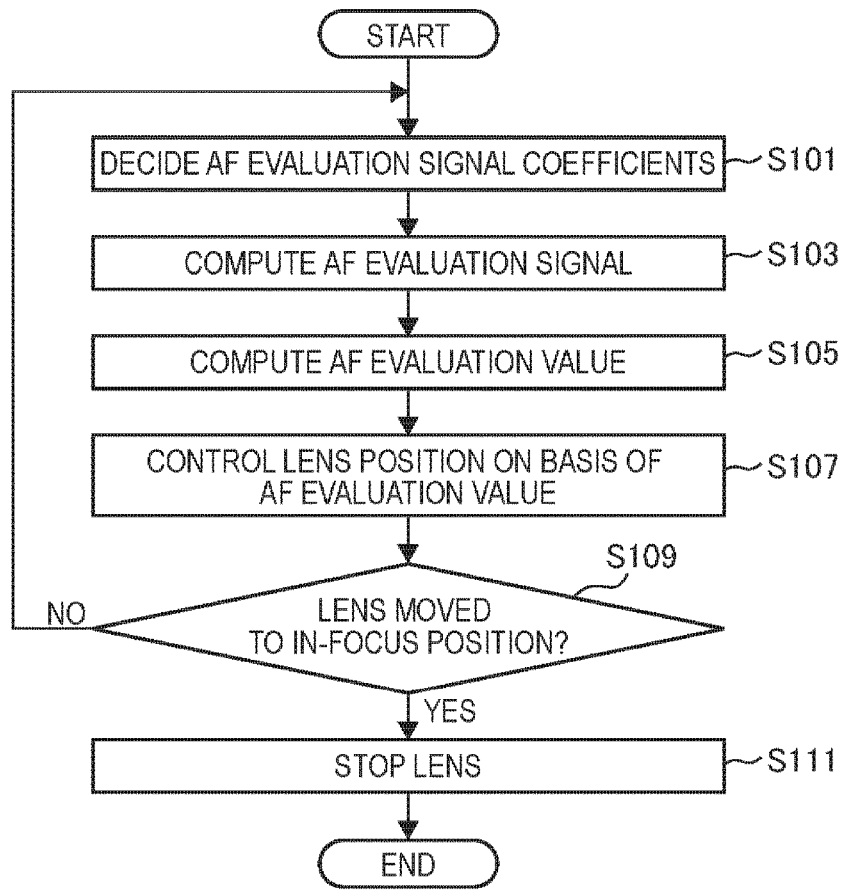
FIG. 6 is a flowchart illustrating an example of the flow of a series of processes by a medical observation device according to the embodiment.

Next, FIG. 6 will be referenced to describe an example of the flow of the sequence of processes by the medical observation device according to the present embodiment, with particular focus on processes related to the AF operation. FIG. 6 is a flowchart illustrating an example of a flow of a series of processes by a medical observation device according to the present embodiment, and in particular, illustrates an example of a flow of processes related to an AF operation by the control section 130.

(Step S101)

The AF evaluation signal computation section 135 of the control section 130 acquires from an input section an observation mode selection signal indicating an observation mode selected by the surgeon (user), and reads out, from a certain storage area, AF evaluation signal coefficients corresponding to the observation mode selection signal. Additionally, as another example, the AF evaluation signal computation section 135 may also compute AF evaluation signal coefficients in accordance with the content of the development process that the imaging signal processing section 131 applies to the imaging signal. According to the above, the AF evaluation signal computation section 135 decides the AF evaluation signal coefficients to apply.

(Step S103)

Next, the AF evaluation signal computation section 135 acquires an imaging signal for each of the spectral components from the imaging signal processing section 131 via the wave detection frame gate 132, applies the decided AF evaluation signal coefficients to the acquired imaging signals to thereby weight the spectral components, and generates an AF evaluation signal. Subsequently, the AF evaluation signal computation section 135 outputs the computed AF evaluation signal to the AF evaluation value computation section 136.

(Step S105)

The AF evaluation value computation section 136 acquires the AF evaluation signal from the AF evaluation signal computation section 135, and computes an AF evaluation value on the basis of the acquired AF evaluation signal. For example, in the case in which the AF method is the contrast method, the AF evaluation value computation section 136 computes a contrast on the basis of the acquired AF evaluation signal as the AF evaluation value. The AF evaluation value computation section 136 outputs the computed AF evaluation value to the optical system control section 134.

(Step S107)

The optical system control section 134 decides the movement direction and the movement amount of the focus lens 113 on the basis of the AF evaluation value output from the AF wave detection section 133. For example, the optical system control section 134 controls the position of the focus lens 113 via the drive system control section 117, while also comparing the AF evaluation values output from the AF wave detection section 133 before and after the movement of the focus lens 113. On the basis of the AF evaluation value comparison result, the optical system control section 134 decides a movement direction and a movement amount of the focus lens 113 so that the focus lens 113 moves on the optical axis in a direction in which the AF evaluation value increases.

Subsequently, the optical system control section 134 outputs information indicating the movement direction and the movement amount of the focus lens 113 decided on the basis of the AF evaluation value comparison result to the drive system control section 117. The drive system control section 117 receives this information, and via the focus lens driving section 116, causes the focus lens 113 to move in the decided movement direction by the decided movement amount.

(Step S109)

The control section 130 continues the series of processes described above until the focus lens 113 moves to a position at which the AF evaluation value is maximized (that is, moves to the in-focus position) (S109, NO).

(Step S111)

Subsequently, when the focus lens 113 moves to the in-focus position (S109, YES), the control section 130 stops the movement of the focus lens 113, and ends the AF operation.

The above thus references FIG. 6 to describe an example of the flow of the sequence of processes by the medical observation device 100 according to the present embodiment, with particular focus on processes related to the AF operation. As above, the medical observation device 100 according to the present embodiment computes an AF evaluation value on the basis of AF evaluation signal coefficients corresponding to a band targeted for observation among the observation target light from the subject, and an imaging signal from the image sensor 114, and conducts a focusing operation (AF operation) on the basis of the computed AF evaluation value. According to such a configuration, the medical observation device 100 according to the present embodiment is capable of controlling the focal position of the imaging optical system 111 in accordance with the band targeted for observation to bring the subject into focus, even in the case of using an optical system with comparatively large chromatic aberration.

5. Modifications

Next, modifications of a medical observation device according to the present embodiment will be described.

(Deciding AF Evaluation Signal Coefficients Corresponding to Development Content)

The medical observation device according to the embodiment described above decides AF evaluation signal coefficients in accordance with an observation mode selected by the surgeon (user), and generates an AF evaluation signal on the basis of the AF evaluation signal coefficients. In contrast, a medical observation device according to a modification computes AF evaluation signal coefficients dynamically, in accordance with the content of the development process applied to the imaging signal (for example, development parameters applied for the white balance adjustment and the color reproduction process, for example).

As a specific example, it is assumed that the medical observation device 100 generates a picture signal by performing a development process (color reproduction process) on an imaging signal output from the image sensor 114 on the basis of the color reproduction matrix $M_1$, as described earlier as (Formula 4). In this case, the medical observation device 100 according to the modification computes AF evaluation signal coefficients on the basis of the color reproduction matrix $M_1$ used in the development process. For example, the formula indicated as (Formula 7) below is an example of a formula for computing AF evaluation signal coefficients based on the color reproduction matrix $M_1$ used in the development process.

[Math. 5]

$$\begin{pmatrix} r \\ g \\ b \end{pmatrix} = M_1 \times A = \begin{pmatrix} m_{00} & m_{01} & m_{02} \\ m_{10} & m_{11} & m_{12} \\ m_{20} & m_{21} & m_{22} \end{pmatrix} \times \begin{pmatrix} k_r \\ k_g \\ k_b \end{pmatrix} \quad \text{(Formula 7)}$$

In (Formula 7) indicated above, $A=(k_r, k_g, k_b)$ is a transformation formula for transforming the development parameters applied for the development process into the AF evaluation signal coefficients, and is decided in accordance with the weights on the spectral components which correspond to the band targeted for observation, for example. As a specific example, the medical observation device 100 may specify the transformation formula A to apply in accordance with an observation mode selected by the surgeon (user) via any of various types of input sections. For example, in the case in which narrow-band imaging, which treats green light and blue light as the observation target from among the observation target light from the subject, is selected, it is sufficient for the medical observation device 100 to select a transformation formula A set so that the coefficients $k_g$ and $k_b$ are larger compared to the coefficient $k_r$, for example. Note that the respective coefficients $k_r$, $k_g$, and $k_b$ in the transformation formula A corresponding to the observation mode may be computed in advance on the basis of prior experiment or the like so that a component in a band targeted for observation in the relevant observation mode is emphasized more strongly, for example.

Also, in the example described above, an example in which the medical observation device 100 computes the AF evaluation signal coefficients applied as the development process is described, but obviously the development parameters to apply to the computation of the AF evaluation signal coefficients may be changed appropriately in accordance with the content of the applied development process. For example, in the case of applying the color reproduction matrix $M_2$ for transforming an RGB signal into components in the YCbCr space as the development process, the medical observation device 100 may compute the AF evaluation signal coefficients by applying the relevant color reproduction matrix $M_2$ to the transformation formula A corresponding to the selected observation mode.

In addition, in the case of applying multiple development parameters as the 6 development process, the medical observation device 100 may compute the AF evaluation signal coefficients by successively multiplying the applied development parameters by the selected transformation formula A. As a specific example, in the case of applying the color reproduction matrices $M_1$ and $M_2$ as the development parameters, the medical observation device 100 may compute the AF evaluation signal coefficients on the basis of the formula labeled (Formula 8) below.

[Math. 6]

$$\begin{pmatrix} r \\ g \\ b \end{pmatrix} = M_1 \times M_2 \times A = \begin{pmatrix} m_{00} & m_{01} & m_{02} \\ m_{10} & m_{11} & m_{12} \\ m_{20} & m_{21} & m_{22} \end{pmatrix} \times \begin{pmatrix} m_{60} & m_{61} & m_{62} \\ m_{70} & m_{71} & m_{72} \\ m_{80} & m_{81} & m_{82} \end{pmatrix} \times \begin{pmatrix} k_r \\ k_g \\ k_b \end{pmatrix} \quad \text{(Formula 8)}$$

Note that, the example indicated above is merely one example, and the units of management of the transformation formula A may be changed appropriately in accordance with the method of operating the medical observation device 100. As a specific example, the medical observation device 100 may decide the transformation formula A in accordance with the surgical procedure of a surgery in which a subject is imaged. Also, as another example, the medical observation device 100 may decide the transformation formula A in accordance with a clinical department in which a subject is imaged.

According to a configuration like the above, the medical observation device 100 according to the modification is capable of controlling the focal position of the imaging optical system 111 in accordance with the content of the development process applied to the imaging signal, to bring the subject into focus with a more favorable aspect.

(Deciding AF Evaluation Signal Coefficients Corresponding to Imaging Optical System)

In addition, the medical observation device 100 may also be configured so that the imaging optical system 111 (or the imaging section 110 itself) is removable. In such a case, there are anticipated cases in which imaging optical systems 111 having different optical characteristics are installed in the medical observation device 100, and there are also anticipated cases in which the in-focus position is different depending on the optical characteristics of the installed imaging optical system 111. Particularly, in a situation of treating multiple bands among the observation target light from the subject (for example, bands positioned close to each other) as observation targets, in the case of controlling the focal position of the imaging optical system 111 so that respective subject images corresponding to each band are in focus, the favorable in-focus position may be different in some cases depending on the optical characteristics of the imaging optical system 111. In light of such a situation, the medical observation device 100 may compute the AF evaluation signal coefficients in accordance with the optical characteristics (for example, the chromatic aberration) of the installed imaging optical system 111.

As a specific example, the transformation formula $A=(k_r, k_g, k_b)$ for computing the AF evaluation signal coefficients described above may be computed for each imaging optical system 111 in accordance with the optical characteristics of the relevant imaging optical system 111 on the basis of prior experiment or the like, and stored in advance in a certain storage area. The medical observation device 100 identifies the installed imaging optical system 111, for example, and on the basis of the identification result, reads out from the certain storage area the transformation formula A corresponding to the relevant imaging optical system 111. Subsequently, the medical observation device 100 may compute AF evaluation signal coefficients on the basis of the read-out transformation formula A.

Note that insofar as the medical observation device 100 can identify the imaging optical system 111 installed in itself, the method is not particularly limited. As a specific example, identification information for identifying an imaging optical system 111 may be stored in advance in a certain storage area of the imaging optical system 111, and the medical observation device 100 may read out the identification information from the storage area of the connected imaging optical system 111 to thereby identify the imaging optical system 111.

Additionally, a transformation formula A may also be set for each band treated as the observation target (in other words, for each observation mode), similarly to the example described above. In this case, for example, a transformation formula A may be computed in advance for each combination of the band treated as the observation target (in other words, the selected observation mode) and the connected imaging optical system 111, and stored in a certain storage area.

Also, as another example, AF evaluation signal coefficients may be computed in advance for each combination of the band treated as the observation target and the connected imaging optical system 111, and stored in a certain storage area. In this case, it is sufficient for the medical observation device 100 to read out from the certain storage area the corresponding AF evaluation signal coefficients, in accordance with the observation mode selected by the surgeon (user) and the identification result regarding the connected imaging optical system 111, for example.

According to a configuration like the above, even in the case of being configured so that the imaging optical system 111 is removable, the medical observation device 100 is capable of controlling the focal position of the imaging optical system 111 in accordance with the optical characteristics of the installed imaging optical system 111, to bring the subject into focus with a more favorable aspect.

6. Applications

Figure 7:
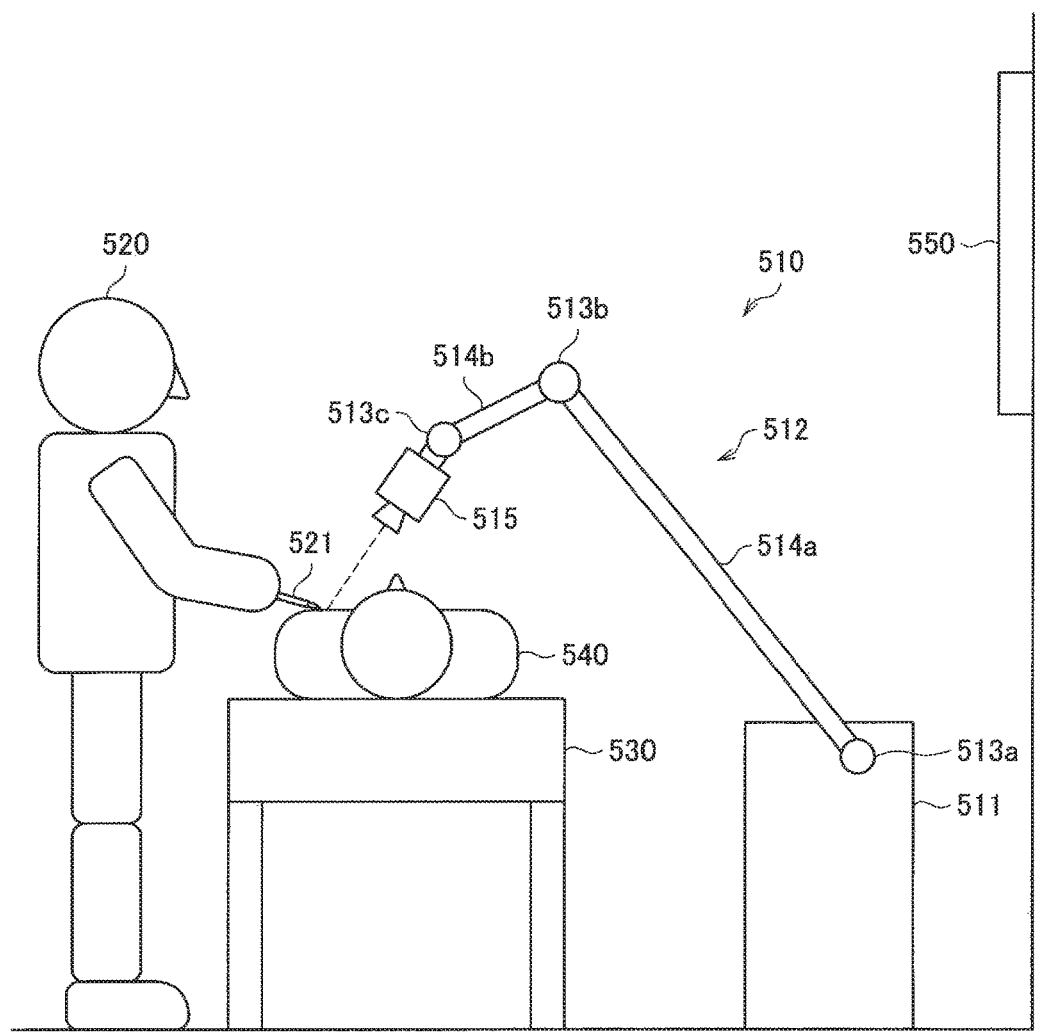
FIG. 7 is an explanatory diagram for explaining an application of a medical observation device according to the embodiment.

Next, FIG. 7 will be referenced to describe an example of a case of using a surgical video microscope device equipped with an arm as another application of a medical observation device according to the present embodiment. FIG. 7 is an explanatory diagram for explaining an application of a medical observation device according to the embodiment.

FIG. 7 diagrammatically illustrates how a medical procedure is performed using a surgical video microscope device. Specifically, referring to FIG. 7, a state is illustrated in which a physician acting as the surgeon (user) 520 is using a surgical tool 521, such as a scalpel, tweezers, or forceps, for example, to perform surgery on an surgery target (patient) 540 lying on an operating table 530. Note that in the following description, medical procedure is used as a collective term to denote various types of medical treatments performed by a physician acting as the user 520 on a patient acting as the surgery target 540, such as a surgery or an examination. Also, although the example illustrated in FIG. 7 illustrates a situation of surgery as an example of a medical procedure, the medical procedure in which the surgical video microscope device 510 is used is not limited to surgery, and may be any of various other types of medical procedures.

Beside the operating table 530, the surgical video microscope device 510 according to the present embodiment is provided. The surgical video microscope device 510 is equipped with a base section 511 which acts as a base, an arm section 512 which extends from the base section 511, and an imaging unit 515 connected as a front edge unit to the front edge of the arm section 512. The arm section 512 includes multiple joint sections 513*a*, 513*b*, and 513*c*, multiple links 514*a* and 514*b* joined by the joint sections 513*a* and 513*b*, and the imaging unit 515 provided on the front edge of the arm section 512. In the example illustrated in FIG. 7, for the sake of simplicity, the arm section 512 includes three joint sections 513*a* to 513*c* and two links 514*a* and 514*b*, but in actuality, the degrees of freedom in the positions and the attitudes of the arm section 512 and the imaging unit 515 may be considered to appropriately configure factors such as the numbers and shapes of the joint sections 513*a* to 513*c* and the links 514*a* and 514*b*, and the directions of the drive axes of the joints 513*a* to 513*c*, so as to achieve the desired degrees of freedom.

The joint sections 513*a* to 513*c* have a function of rotatably joining the links 514*a* and 514*b* to each other, and by driving the rotation of the joint sections 513*a* to 513*c*, the driving of the arm section 512 is controlled.

On the front edge of the arm section 512, the imaging unit 515 is connected as a front edge unit. The imaging unit 515 is a unit that acquires an image of an imaging target, such as a camera capable of capturing a moving image or a still image, for example. As illustrated in FIG. 7, the attitudes and the positions of the arm section 512 and the imaging unit 515 are controlled by the surgical video microscope device 510 so that the imaging unit 515 provided on the front edge of the arm section 512 captures the operating site of the surgery target 540. Note that the configuration of the imaging unit 515 connected as the front edge unit to the front edge of the arm section 512 is not particularly limited, and the imaging unit 515 may be configured as an endoscope or a microscope, for example. Additionally, the imaging unit 515 may also be configured to be removable from the arm section 512. According to such a configuration, an imaging unit 515 depending on the usage scenario may be connected appropriately to the front edge of the arm section 512 as the front edge unit, for example. Note that although the description herein focuses on a case in which the imaging unit 515 is applied as the front edge unit, obviously the front edge unit connected to the front edge of the arm section 512 is not necessarily limited to the imaging unit 515.

Also, at a position facing the user 520, a display device 550 such as a monitor or a display is installed. An image of the operating site acquired by the imaging unit 515 is subjected to various types of image processing by an image processing device (illustration omitted) built into or externally attached to the surgical video microscope device 510, and then displayed on a display screen of the display device 550 as an electronic image. According to such a configuration, the user 520 becomes able to perform various treatments (such as surgery, for example) while looking at an electronic image of the operating site displayed on the display screen of the display device 550.

Note that in the example illustrated in FIG. 7, the imaging unit 515 includes the imaging section 110 discussed earlier with reference to FIG. 4, for example. Also, the image processing device that performs various types of image processing on an image of the operating site acquired by the imaging unit 515 corresponds to an example of the control section 130 discussed earlier with reference to FIG. 4. Additionally, the display device 550 may correspond to an example of an output destination of a picture signal from the control section 130.

The above thus references FIG. 7 to describe an example of a case of using a surgical video microscope device equipped with an arm as another application of a medical observation device according to the present embodiment.

7. Hardware Configuration

Figure 8:
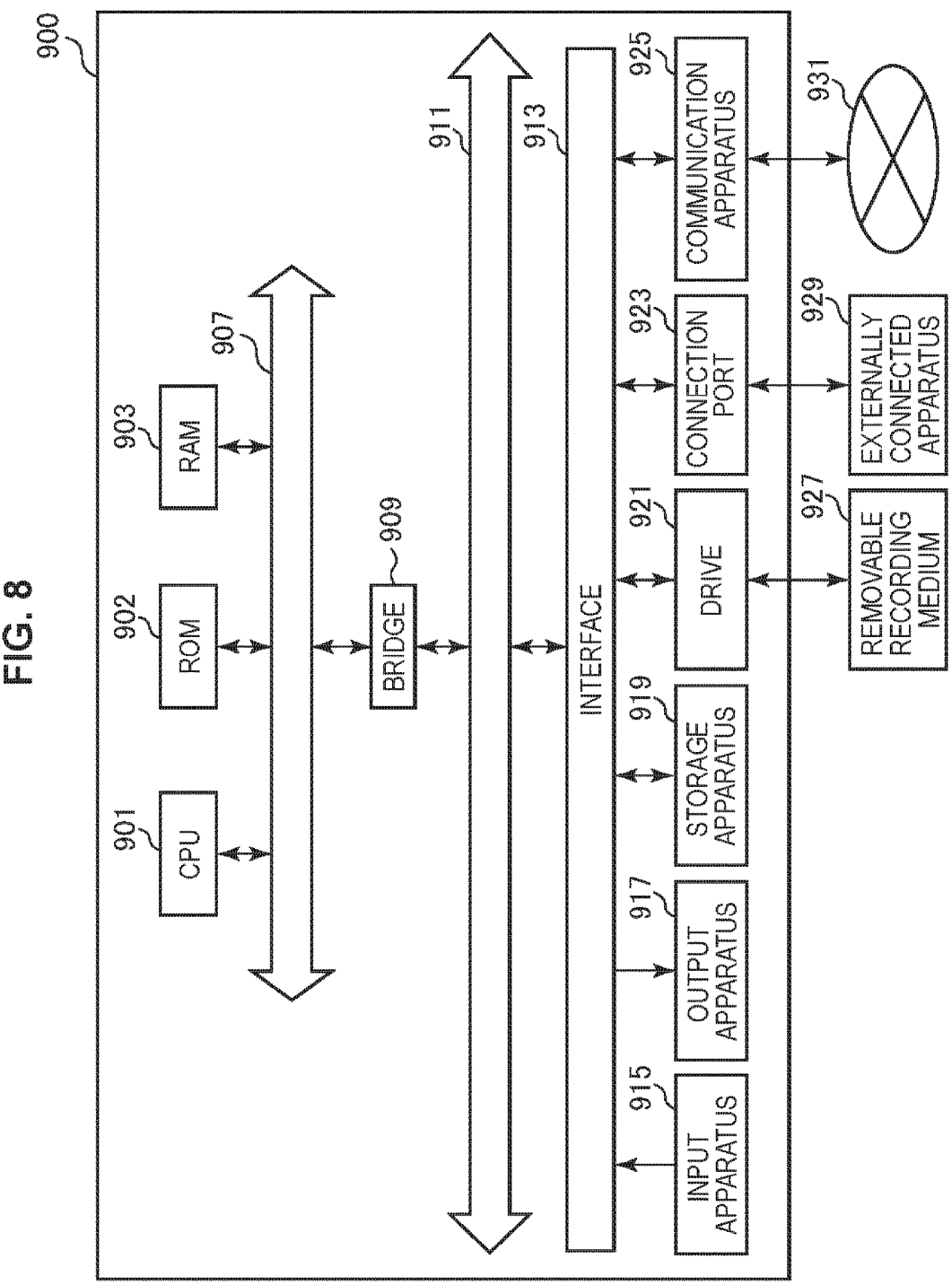
FIG. 8 is a function block diagram illustrating an example configuration of the hardware configuration of an information processing device configured as a medical observation device according to the embodiment.

Next, an example of a hardware configuration of an information processing apparatus 900 configured as a medical observation device according to the present embodiment will be described in detail with reference to FIG. 8. FIG. 8 is a function block diagram illustrating an example configuration of the hardware configuration of an information processing apparatus 900 configured as a medical observation device according to an embodiment of the present disclosure.

As illustrated in FIG. 8, the information processing apparatus 900 mainly includes a CPU 901, a ROM 903, and a RAM 905. Furthermore, the information processing apparatus 900 also includes a host bus 907, a bridge 909, an external bus 911, an interface 913, an input apparatus 915, an output apparatus 917, and a storage apparatus 919. Furthermore, the information processing apparatus 900 also includes a drive 921, a connection port 923, and a communication apparatus 925.

The CPU 901 serves as an arithmetic processing apparatus and a control apparatus, and controls the overall operation or a part of the operation of the information processing apparatus 900 according to various programs recorded in the ROM 903, the RAM 905, the storage apparatus 919, or a removable recording medium 927. The ROM 903 stores programs, operation parameters, and the like used by the CPU 901. The RAM 905 primarily stores programs that the CPU 901 uses and parameters and the like varying as appropriate during the execution of the programs. These are connected with each other via the host bus 907 including an internal bus such as a CPU bus or the like. Note that the respective components of the control section 130 discussed earlier with reference to FIG. 4 may be realized by the CPU 901, for example.

The host bus 907 is connected to the external bus 911 such as a PCI (Peripheral Component Interconnect/Interface) bus via the bridge 909. Additionally, the input apparatus 915, the output apparatus 917, the storage apparatus 919, the drive 921, the connection port 923, and the communication apparatus 925 are connected to the external bus 911 via the interface 913.

The input apparatus 915 is an operation mechanism operated by a user, such as a mouse, a keyboard, a touch panel, buttons, a switch, a lever, or a pedal. Also, the input apparatus 915 may be a remote control mechanism (a so-called remote control) using, for example, infrared light or other radio waves, or may be an externally connected apparatus 929 such as a mobile phone or a PDA conforming to the operation of the information processing apparatus 900. Furthermore, the input apparatus 915 generates an input signal based on, for example, information which is input by a user with the above operation mechanism, and includes an input control circuit for outputting the input signal to the CPU 901. The user of the information processing apparatus 900 can input various data to the information processing apparatus 900 and can instruct the information processing apparatus 900 to perform processing by operating the input apparatus 915.

The output apparatus 917 includes a device capable of visually or audibly notifying acquired information to a user. Examples of such device include display apparatuses such as a CRT display apparatus, a liquid crystal display apparatus, a plasma display apparatus, an EL display apparatus and lamps, audio output apparatuses such as a speaker and a headphone, a printer, and the like. For example, the output apparatus 917 outputs a result obtained by various processes performed by the information processing apparatus 900. More specifically, the display apparatus displays, in the form of texts or images, a result obtained by various processes performed by the information processing apparatus 900. On the other hand, the audio output apparatus converts an audio signal including reproduced audio data and sound data into an analog signal, and outputs the analog signal. For example, the output apparatus 917 configured as a display apparatus may be anticipated as an output destination of a picture signal from the imaging signal processing section 131 described earlier with reference to FIG. 4.

The storage apparatus 919 is a device for storing data configured as an example of a storage unit of the information processing apparatus 900. The storage apparatus 919 is configured from, for example, a magnetic storage device such as a HDD (Hard Disk Drive), a semiconductor storage device, an optical storage device, or a magneto-optical storage device. This storage apparatus 919 stores programs to be executed by the CPU 901, and various data.

The drive 921 is a reader/writer for recording medium, and is embedded in the information processing apparatus 900 or attached externally thereto. The drive 921 reads information recorded in the attached removable recording medium 927 such as a magnetic disk, an optical disc, a magneto-optical disk, or a semiconductor memory, and outputs the read information to the RAM 905. Furthermore, the drive 921 can write record in the attached removable recording medium 927 such as a magnetic disk, an optical disc, a magneto-optical disk, or a semiconductor memory. The removable recording medium 927 is, for example, a DVD medium, an HD-DVD medium, or a Blu-ray (a registered trademark) medium. In addition, the removable recording medium 927 may be a CompactFlash (CF; a registered trademark), a flash memory, an SD memory card (Secure Digital Memory Card), or the like. Alternatively, the removable recording medium 927 may be, for example, an IC card (Integrated Circuit Card) equipped with a non-contact IC chip or an electronic appliance.

The connection port 923 is a port for allowing apparatuses to directly connect to the information processing apparatus 900. Examples of the connection port 923 include a USB (Universal Serial Bus) port, an IEEE1394 port, a SCSI (Small Computer System Interface) port, and the like. Other examples of the connection port 923 include an RS-232C port, an optical audio terminal, an HDMI (a registered trademark) (High-Definition Multimedia Interface) port, and the like. By the externally connected apparatus 929 connecting to this connection port 923, the information processing apparatus 900 directly obtains various types of data from the externally connected apparatus 929 and provides various types of data to the externally connected apparatus 929.

The communication apparatus 925 is a communication interface including, for example, a communication device for connecting to a communication network 931. The communication apparatus 925 is, for example, a wired or wireless LAN (Local Area Network), Bluetooth (registered trademark), a communication card for WUSB (Wireless USB), or the like. Alternatively, the communication apparatus 925 may be a router for optical communication, a router for ADSL (Asymmetric Digital Subscriber Line), a modem for various communications, or the like. This communication apparatus 925 can transmit and receive signals and the like in accordance with a predetermined protocol such as TCP/IP on the Internet and with other communication apparatuses, for example. The communication network 931 connected to the communication apparatus 925 includes a network and the like, which is connected via wire or wirelessly, and may be, for example, the Internet, a home LAN, infrared communication, radio wave communication, satellite communication, or the like.

Heretofore, an example of the hardware configuration capable of realizing the functions of the information processing apparatus 900 included in a medical stereoscopic observation system according to the embodiment of the present disclosure has been shown. Each of the structural elements described above may be configured using a general-purpose material, or may be implemented by hardware dedicated to the function of each structural element. Accordingly, the hardware configuration to be used can be changed as appropriate according to the technical level at the time of carrying out the present embodiment. Note that, although not shown in FIG. 8, for example, it naturally includes various configurations corresponding to the medical observation device described above.

Note that it is also possible to develop a computer program for realizing the respective functions of the information processing apparatus 900 included in a medical stereoscopic observation system according to the present embodiment as discussed above, and implement the computer program in a personal computer or the like. In addition, a computer-readable recording medium storing such a computer program may also be provided. The recording medium may be a magnetic disk, an optical disc, a magneto-optical disk, or flash memory, for example. Furthermore, the above computer program may also be delivered via a network, for example, without using a recording medium.

8. Conclusion

Thus, as described above, the medical observation device 100 according to the present embodiment computes an AF evaluation value on the basis of AF evaluation signal coefficients corresponding to a band targeted for observation among the observation target light from the subject, and an imaging signal from the image sensor 114, and conducts a focusing operation (AF operation) on the basis of the computed AF evaluation value. According to such a configuration, the medical observation device 100 according to the present embodiment is capable of controlling the focal position of the imaging optical system 111 in accordance with the band targeted for observation to bring the subject into focus, even in the case of using an optical system with comparatively large chromatic aberration. In other words, according to the medical observation device 100 according to the present embodiment, the surgeon (user) becomes able to observe a clearer subject image corresponding to a band targeted for observation, even with what is called specific light observation.

Particularly, for example, the medical observation device 100 according to the present embodiment is able to generate an AF evaluation signal on the basis of AF evaluation signal coefficients corresponding to the characteristics of a development process applied to an imaging signal from the image sensor 114, and compute an AF evaluation value on the basis of the AF evaluation signal. According to such a configuration, even in a situation of performing development focusing on each of multiple different bands, the medical observation device 100 is capable of controlling the focal length of the imaging optical system 111 to bring the subject into focus for each of the multiple bands.

As a more specific example, consider a case in which the medical observation device 100 irradiates a subject with auxiliary light in multiple different bands from a light source, and for each of the multiple bands, performs a different development process on an imaging signal based on the light receiving result regarding reflected light from the subject. In this case, for example, the medical observation device 100 generates an AF evaluation signal for each development process on the basis of the AF evaluation signal coefficients for each development process focusing on each of the multiple bands, and computes an AF evaluation value on the basis of the relevant AF evaluation signal. Additionally, for each development process, the medical observation device 100 may control the focal position of the imaging optical system 111 on the basis of the AF evaluation value corresponding to the relevant development process. According to such control, the medical observation device 100 becomes able to output an image that is in focus (that is, an image in which the affected area is presented more clearly) with respect to each of different positions in vivo, such as at the surface of the affected area and in the interior of the affected area, for example.

Also, as another example, in the case of observing a phosphor that emits fluorescence in multiple bands, consider a case in which, for each of the multiple bands, the medical observation device 100 performs a different development process for each band on an imaging signal based on a light receiving result regarding the fluorescence. Even in such a case, for example, the medical observation device 100 may compute an AF evaluation value on the basis of AF evaluation signal coefficients for each development process focusing on each of the multiple bands, and for each development process, the medical observation device 100 may control the focal position of the imaging optical system 111 on the basis of the AF evaluation value corresponding to the relevant development process. According to such control, the medical observation device 100 becomes able to output an image that is in focus (that is, an image in which each site is presented more clearly) with respect to each of different sites in vivo (in other words, portions that emit mutually different fluorescence), such as blood vessels and a tumor site, for example.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A medical observation device including:

a computation section that applies, to an imaging signal corresponding to each of a plurality of different spectral components based on a light receiving result regarding observation target light from a subject in vivo from an image sensor, weights of the plurality of spectral components corresponding to a band targeted for observation from among bands in the observation target light, and computes an evaluation value indicating a degree of being in-focus on a basis of the imaging signal to which the weights are applied; and a control section that controls, on a basis of the evaluation value, a position of at least one optical member in an optical system that forms an image of the observation target light from the subject onto the image sensor, and thereby controls a focal position of the optical system.

(2)

The medical observation device according to (1), in which the computation section computes the evaluation value on a basis of the weights corresponding to a correction parameter for generating image data based on a component in the band targeted for observation on a basis of the plurality of spectral components.

(3)

The medical observation device according to (1), in which the computation section computes the evaluation value on a basis of the weights set in advance for each band targeted for observation.

(4)

The medical observation device according to (3), in which the computation section acquires the weights corresponding to the mode that is selected from among the weights set in advance for each of a plurality of modes that treat at least part of the bands in the observation target light as the observation target, and computes the evaluation value on the basis of the acquired weights.

(5)

The medical observation device according to (4), in which a mode corresponding to at least any of narrow-band imaging, auto fluorescence imaging, and infra red imaging is included in the plurality of modes.

(6)

The medical observation device according to (1), in which the computation section computes the evaluation value on a basis of the weights set in accordance with a surgical procedure of a surgery in which the subject is imaged.

(7)

The medical observation device according to (1), in which the computation section computes the evaluation value on a basis of the weights set in accordance with a clinical department in which the subject is imaged.

(8)

The medical observation device according to any one of (1) to (7), in which
the computation section computes the evaluation value on a basis of the weights set in accordance with an optical characteristic of the optical system.

(9)

The medical observation device according to any one of (1) to (8), in which
the imaging signal corresponding to the plurality of spectral components is an RGB signal, and
when R, G, and B are luminance components of an R signal, a G signal, and a B signal, respectively, and r, g, and b are coefficients based on the weights and corresponding to the R signal, the G signal, and the B signal, respectively, an evaluation signal L for computing the evaluation value is computed on a basis of a formula listed below:

$$L = r \times R + g \times G + b \times B \qquad \text{[Math. 7]}$$

(10)

The medical observation device according to any one of (1) to (9), in which
the control section controls the focal position of the optical system on a basis of contrast in a subject image computed on a basis of the evaluation value.

(11)

The medical observation device according to any one of (1) to (10), including:
an imaging section that includes the image sensor.

(12)

The medical observation device according to (11), in which
the imaging section is an endoscope configured to be inserted into a body cavity of a patient.

(13)

The medical observation device according to (11), in which
the imaging section is a microscope section that includes the optical system configured to acquire an optical image of the subject, and
the medical observation device further includes:
a support section that supports the microscope section.

(14)

A medical observation method that is executed by a processor, the medical observation method including:
applying, to an imaging signal corresponding to each of a plurality of different spectral components based on a light receiving result regarding observation target light from a subject in vivo from an image sensor, weights of the plurality of spectral components corresponding to a band targeted for observation from among bands in the observation target light, and computing an evaluation value indicating a degree of being in-focus on a basis of the imaging signal to which the weights are applied; and
controlling, on a basis of the evaluation value, a position of at least one optical member in an optical system that forms an image of the observation target light from the subject onto the image sensor, and thereby controlling a focal position of the optical system.

REFERENCE SIGNS LIST 1 endoscopic surgical system
11 endoscope
13 CCU
15 display device
17 light source device
21 treatment tool device
22 energy treatment tool
23 forceps
24 pneumoperitoneum device
25a, 25b trocar
26 recorder
27 printer
31 cart
33 patient bed
35 footswitch
100 medical observation device
110 imaging section
111 imaging optical system
112 zoom lens
113 focus lens
114 image sensor
115 zoom lens driving section
116 focus lens driving section
117 drive system control section
118 image sensor driving section
130 control section
131 imaging signal processing section
132 wave detection frame gate
133 wave detection section
134 optical system control section
135 evaluation signal computation section
136 evaluation value computation section
170 light source section

The invention claimed is:

1. A medical observation device comprising:
a computation section that applies, to an imaging signal corresponding to each of a plurality of different spectral components based on a light receiving result regarding observation target light from a subject in vivo from an image sensor, weights of the plurality of spectral components corresponding to a band targeted for observation from among bands in the observation target light, and computes an evaluation value indicating a degree of being in-focus on a basis of the imaging signal to which the weights are applied; and a control section that controls, on a basis of the evaluation value, a position of at least one optical member in an optical system that forms an image of the observation target light from the subject onto the image sensor, and thereby controls a focal position of the optical system.

2. The medical observation device according to claim 1, wherein
the computation section computes the evaluation value on a basis of the weights corresponding to a correction parameter for generating image data based on a component in the band targeted for observation on a basis of the plurality of spectral components.

3. The medical observation device according to claim 1, wherein
the computation section computes the evaluation value on a basis of the weights set in advance for each band targeted for observation.

4. The medical observation device according to claim 3, wherein
the computation section acquires the weights corresponding to the mode that is selected from among the weights set in advance for each of a plurality of modes that treat at least part of the bands in the observation target light as the observation target, and computes the evaluation value on the basis of the acquired weights.

5. The medical observation device according to claim 1, wherein
the imaging signal corresponding to the plurality of spectral components is an RGB signal, and
when R, G, and B are luminance components of an R signal, a G signal, and a B signal, respectively, and r, g, and b are coefficients based on the weights and corresponding to the R signal, the G signal, and the B signal, respectively, an evaluation signal L for computing the evaluation value is computed on a basis of a formula listed below:

$$L=r\times R+g\times G+b\times B.$$

6. The medical observation device according to claim 1, wherein
the control section controls the focal position of the optical system on a basis of contrast in a subject image computed on a basis of the evaluation value.

7. The medical observation device according to claim 1, comprising:
an imaging section that includes the image sensor, wherein
the imaging section is a microscope section that includes the optical system configured to acquire an optical image of the subject, and
the medical observation device further comprises:
a support section that supports the microscope section.

8. A medical observation device comprising:
circuitry configured to
apply, to an imaging signal corresponding to each of a plurality of different spectral components based on a light receiving result regarding observation target light from a subject in vivo from an image sensor, weights corresponding to each of the plurality of spectral components;

compute an evaluation value indicating a degree of focus on a basis of the imaging signal to which the weights are applied; and
control, on a basis of the evaluation value, a position of at least one optical member in an optical system that forms an image of the observation target light from the subject onto the image sensor.

9. The medical observation device according to claim 8, wherein
the circuitry is configured to compute the evaluation value on a basis of the weights set in advance for each band targeted for observation from among bands in the observation target light.

10. The medical observation device according to claim 9, wherein the circuitry is configured to:
acquire the weights corresponding to a mode that is selected from among weights set in advance for each of a plurality of modes that treat at least part of the bands in the observation target light as the observation target; and
compute the evaluation value on the basis of the acquired weights.

11. The medical observation device according to claim 10, wherein
a mode corresponding to at least any of narrow-band imaging, auto fluorescence imaging, and infrared imaging is included in the plurality of modes.

12. The medical observation device according to claim 8, wherein
the circuitry is configured to compute the evaluation value on a basis of the weights set in accordance with a surgical procedure of a surgery in which the subject is imaged.

13. The medical observation device according to claim 8, wherein
the circuitry is configured to compute the evaluation value on a basis of the weights set in accordance with a clinical department in which the subject is imaged.

14. The medical observation device according to claim 8, wherein
the circuitry is configured to compute the evaluation value on a basis of the weights set in accordance with an optical characteristic of the optical system.

15. The medical observation device according to claim 8, wherein
the imaging signal corresponding to the plurality of spectral components is an RGB signal, and
when R, G, and B are luminance components of an R signal, a G signal, and a B signal, respectively, and r, g, and b are coefficients based on the weights and corresponding to the R signal, the G signal, and the B signal, respectively, an evaluation signal L for computing the evaluation value is computed on a basis of a formula listed below:

$$L=r\times R+g\times G+b\times B.$$

16. The medical observation device according to claim 8, wherein
the circuitry is configured to control the focal position of the optical system on a basis of contrast in a subject image computed on a basis of the evaluation value.

17. The medical observation device according to claim 8, comprising:
a camera head that includes the image sensor.

18. The medical observation device according to claim 8, comprising:

an endoscope including the image sensor, wherein the endoscope is configured to be inserted into a body cavity of a patient.

19. The medical observation device according to claim 8, comprising:
- a microscope including the image sensor and the optical system configured to acquire an optical image of the subject; and
- a support structure that supports the microscope.

20. A medical observation method that is executed by a medical observation device, the medical observation method comprising:
- applying, to an imaging signal corresponding to each of a plurality of different spectral components based on a light receiving result regarding observation target light from a subject in vivo from an image sensor, weights corresponding to each of the plurality of spectral components;
- computing an evaluation value indicating a degree of focus on a basis of the imaging signal to which the weights are applied; and
- controlling, on a basis of the evaluation value, a position of at least one optical member in an optical system that forms an image of the observation target light from the subject onto the image sensor.

* * * * *